(12) United States Patent
Lee et al.

(10) Patent No.: US 10,702,041 B2
(45) Date of Patent: Jul. 7, 2020

(54) PACT-TYPE COSMETICS AND CONTAINERS THEREFOR

(71) Applicant: KPT LTD, Chungcheongbuk-do (KR)

(72) Inventors: Jae-Uk Lee, Daejeon (KR); Yanfu Jiang, Cheongju-si (KR); Taeck-Hyun Jeong, Cheongju-si (KR); Byung-Ho Park, Chungcheongbuk-do (KR)

(73) Assignee: KPT LTD, Chungcheongbuk-do (KR)

( * ) Notice: Subject to any disclaimer, the term of this patent is extended or adjusted under 35 U.S.C. 154(b) by 124 days.

(21) Appl. No.: 15/365,926

(22) Filed: Nov. 30, 2016

(65) Prior Publication Data

US 2017/0079408 A1  Mar. 23, 2017

Related U.S. Application Data

(63) Continuation-in-part of application No. PCT/KR2016/006372, filed on Jun. 6, 2016.

(30) Foreign Application Priority Data

Jul. 9, 2015  (KR) .................. 10-2015-0097585

(51) Int. Cl.
*A45D 40/00* (2006.01)
*A45D 33/02* (2006.01)
(Continued)

(52) U.S. Cl.
CPC ....... *A45D 40/0068* (2013.01); *A45D 33/025* (2013.01); *A45D 40/22* (2013.01); *A61K 8/02* (2013.01); *A61K 8/0204* (2013.01); *A61K 8/19* (2013.01); *A61K 8/26* (2013.01); *A61K 8/27* (2013.01); *A61K 8/29* (2013.01); *A61K 8/30* (2013.01); *A61K 8/34* (2013.01); *A61K 8/342* (2013.01); *A61K 8/345* (2013.01); *A61K 8/365* (2013.01); *A61K 8/37* (2013.01); *A61K 8/44* (2013.01); *A61K 8/4946* (2013.01); *A61K 8/585* (2013.01); *A61K 8/60* (2013.01); *A61K 8/673* (2013.01); *A61K 8/675* (2013.01); *A61K 8/678* (2013.01); *A61K 8/73* (2013.01);
(Continued)

(58) Field of Classification Search
None
See application file for complete search history.

(56) References Cited

U.S. PATENT DOCUMENTS

| | | | | |
|---|---|---|---|---|
| 5,107,871 A | * | 4/1992 | Butcher | A45D 33/006 132/293 |
| 5,804,203 A | * | 9/1998 | Hahn | A61K 8/19 424/401 |

(Continued)

FOREIGN PATENT DOCUMENTS

| KR | 1020090100643 A | 9/2009 |
|---|---|---|
| KR | 1020120108509 A | 10/2012 |

(Continued)

*Primary Examiner* — Monica A Shin
(74) *Attorney, Agent, or Firm* — Lucas & Mercanti, LLP

(57) ABSTRACT

The present invention relates to a cosmetic comprising a cosmetic composition of bead-type liquid foundation filled in a mesh net equipped cosmetic container. This cosmetic maintains portability as the conventional cushion-type cosmetic has and at the same time is more advantageous in preventing the loss of cosmetic ingredients because urethane foam is not used as a carrier for the cosmetic composition herein.

10 Claims, 12 Drawing Sheets cosmetic composition of bead-type

+ mesh net equipped cosmetic container pact-type cosmetic

(51) Int. Cl.
    *A61Q 19/00*     (2006.01)
    *A61K 8/30*     (2006.01)
    *A61K 8/34*     (2006.01)
    *A61K 8/89*     (2006.01)
    *A61K 8/02*     (2006.01)
    *A61Q 17/04*     (2006.01)
    *A61Q 1/02*     (2006.01)
    *A61K 8/92*     (2006.01)
    *A61K 8/898*     (2006.01)
    *A61K 8/86*     (2006.01)
    *A61K 8/81*     (2006.01)
    *A61K 8/73*     (2006.01)
    *A61K 8/67*     (2006.01)
    *A61K 8/60*     (2006.01)
    *A61K 8/58*     (2006.01)
    *A61K 8/49*     (2006.01)
    *A61K 8/44*     (2006.01)
    *A61K 8/37*     (2006.01)
    *A61K 8/365*     (2006.01)
    *A61K 8/27*     (2006.01)
    *A61K 8/26*     (2006.01)
    *A45D 40/22*     (2006.01)
    *A61K 8/19*     (2006.01)
    *A61K 8/29*     (2006.01)
    *A45D 34/00*     (2006.01)
    *A61K 8/97*     (2017.01)

(52) U.S. Cl.
    CPC ............ *A61K 8/731* (2013.01); *A61K 8/8105* (2013.01); *A61K 8/8152* (2013.01); *A61K 8/86* (2013.01); *A61K 8/89* (2013.01); *A61K 8/898* (2013.01); *A61K 8/922* (2013.01); *A61K 8/97* (2013.01); *A61Q 1/02* (2013.01); *A61Q 17/04* (2013.01); *A61Q 19/00* (2013.01); A61K 2800/43 (2013.01); A61K 2800/48 (2013.01); A61K 2800/594 (2013.01); A61K 2800/87 (2013.01)

(56) References Cited

U.S. PATENT DOCUMENTS

| | | | |
|---|---|---|---|
| 2004/0009131 A1* | 1/2004 | Simonnet | A61K 8/064 424/63 |
| 2006/0292193 A1* | 12/2006 | Lee | A61K 8/044 424/401 |
| 2007/0167338 A1* | 7/2007 | McHugh | A61K 8/0237 510/130 |
| 2009/0010863 A1* | 1/2009 | Barton | A61K 8/44 424/64 |
| 2011/0159060 A1* | 6/2011 | Khan | A61K 8/0287 424/401 |
| 2015/0352017 A1* | 12/2015 | Foley | A61K 8/064 424/60 |

FOREIGN PATENT DOCUMENTS

| | | |
|---|---|---|
| KR | 1020130083852 A | 7/2013 |
| KR | 10-1477583 B1 | 12/2014 |
| KR | 101474279 B1 | 12/2014 |
| KR | 1020140144264 A | 12/2014 |
| KR | 10-2015-0061234 A | 6/2015 |

* cited by examiner

A Type

B Type

C Type

PACT-TYPE COSMETICS AND CONTAINERS THEREFOR

CROSS-REFERENCE TO RELATED APPLICATIONS

This patent application is a continuation-in-part of PCT International Application No. PCT/KR2016/006372 filed Jun. 6, 2016, which claims priority of Korean Patent Application No. 10-2015-0097585, filed Jul. 9, 2015, the entire contents of each of which are incorporated herein by reference.

BACKGROUND OF THE INVENTION

Field of the Disclosure

The present disclosure relates to pact-typed cosmetics. The pact-typed cosmetic is a bead-type liquid foundation cosmetic composition disposed within in a mesh net-equipped container.

Description of the Potentially Related Art

Conventional liquid cosmetic compositions are typically disposed in a vacuum container, a pump-type container, or a glass container. The containers are then typically distributed and stored before acquisition by a consumer. However, the containers are not easy to carry, so studies relating to liquid cosmetic compositions that are easy to carry have been undertaken.

A pact-type container is an example of a container that carries a liquid cosmetic composition. There are various considerations in filling a pact-type container with a liquid cosmetic composition, for example, whether a carrier for a liquid cosmetic composition is suitable for the pact-type container, whether the carrier is suitable for carrying the liquid cosmetic composition, whether the carrier can maintain the cosmetic composition evenly for a long period of time, and whether the cosmetic composition included in the carrier can be released at a proper time in a proper amount. An ideal carrier for such a cosmetic composition would be suitable for the pact-type container considering all of the above.

Patent reference 1 (Korean Patent Publication No. 10-2013-0083852) describes a carrier for a cosmetic composition containing a foamed urethane layer-structure and a cosmetic.

Patent reference 2 (Korean Patent Publication No. 10-2009-0100643) describes a cosmetic composition filled in a pact-type container, wherein the cosmetic composition is a W/O (water in oil) type UV blocking composition with low viscosity. The W/O type UV blocking composition with low viscosity is impregnated in urethane foam, which is packed in a pact-type container.

Patent reference 3 (Korean Patent Publication No. 10-2012-0108509) discloses a study attempting to improve the physical properties of a cosmetic composition carrier including urethane foam.

However, the cushion-type products using urethane foam of Patent references 1-3 have a problem of big cosmetic composition loss. For example, the basic structure of the cushion-type cosmetic results in the wasteful impregnation of a cosmetic composition in the foam.

Therefore, there is a long felt but unsolved need for a portable cosmetic that minimizes cosmetic composition loss and has equal convenience in portability to the conventional cushion-type products.

Patent reference 4 (Korean Patent Publication No. 10-2014-0144264) discloses a method of preparing a bead-type cosmetic composition based on the idea that produces ball type ice-cream via cryogenic freezing in the field of food industry.

SUMMARY OF THE INVENTION

It is an object of the present disclosure to provide a cosmetic that is not only as portable as the conventional cushion-type products but also minimizes cosmetic ingredient loss.

To achieve the above object, disclosed is a pact-type cosmetic, wherein the bead-type liquid foundation cosmetic composition is 0.1-1.0% weight/volume (w/v) gel forming material; 10-20% w/v oil component; 50-60% w/v water component; 1-10% w/v thickener; 1-10% w/v coloring agent; and 15-25% w/v emulsifier. Disclosed is a pact-type cosmetic disposed in a cosmetic container having a body and a lid, in which a mesh is disposed on the top of the body of the cosmetic container.

The disclosed pact-type cosmetic disposed in the body of the cosmetic container not only maintains the portability of the conventional cushion-type products but also minimizes the loss of the pact-type cosmetic because urethane foam is not used as a carrier for the pact-type cosmetic.

DETAILED DESCRIPTION OF THE DISCLOSURE

Figure 1:
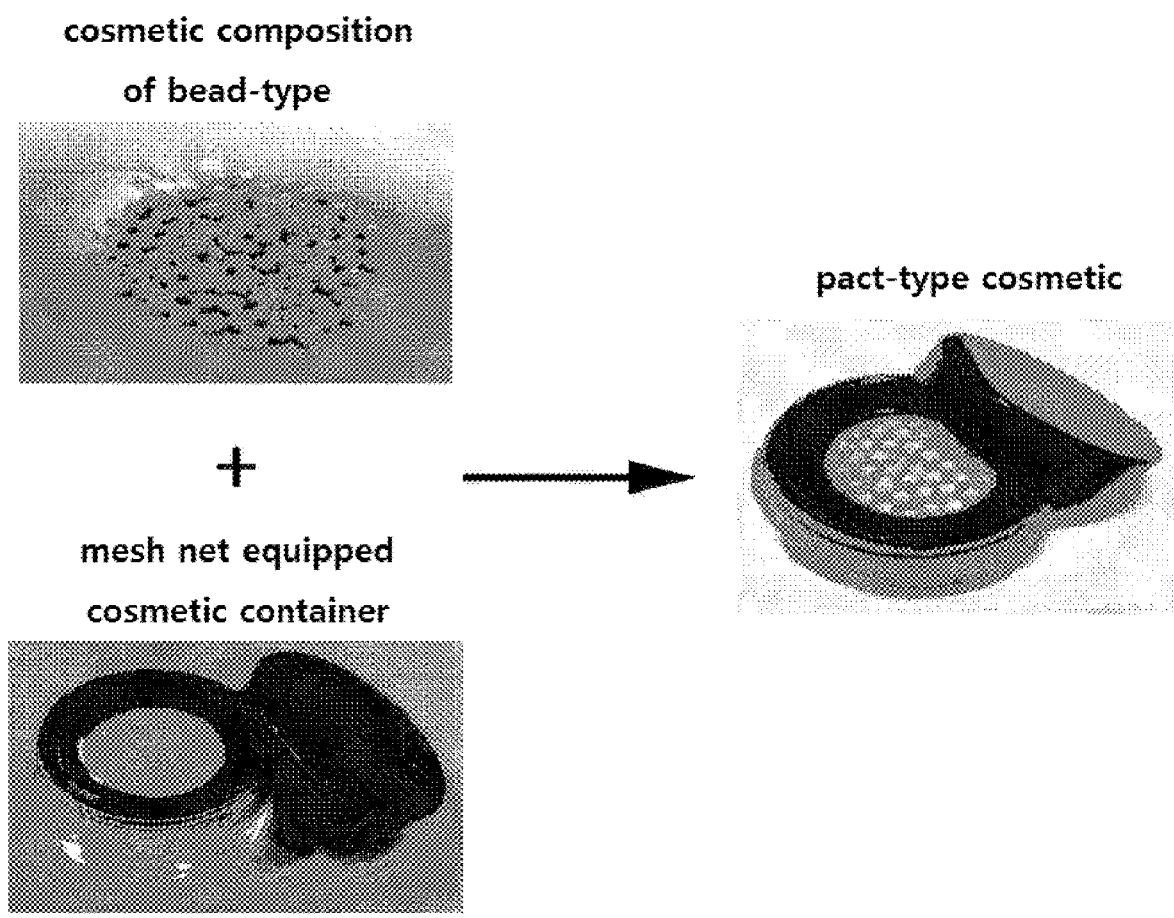
FIG. 1 is a schematic of a pact-type cosmetic and a cosmetic container.
Figure 2:
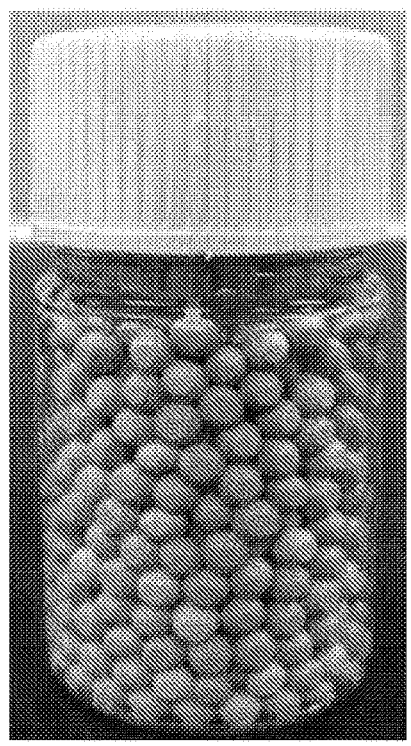
FIG. 2 is an image of the bead-type BB cream prepared in Manufacturing Example 1 at 25° C.
Figure 3:
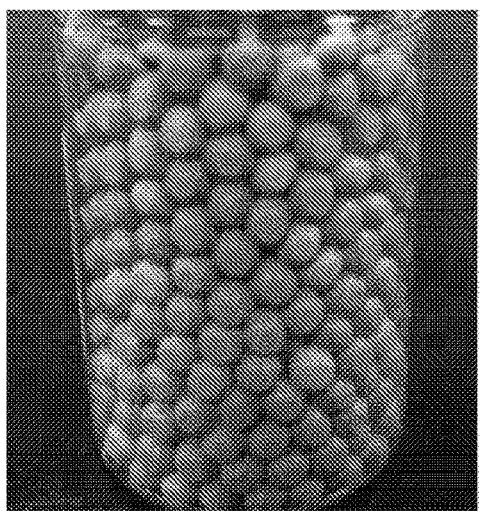
FIG. 3 is an image of the bead-type BB cream prepared in Manufacturing Example 1 after eight weeks at 25° C.
Figure 4:
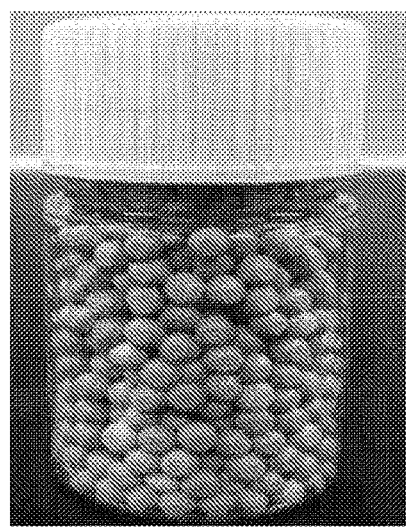
FIG. 4 is an image of the bead-type BB cream prepared in Manufacturing Example 1 at 50° C.
Figure 5:
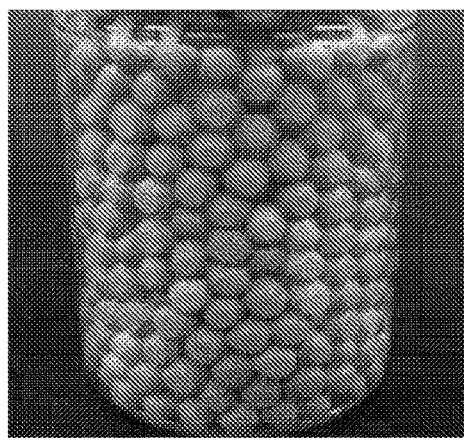
FIG. 5 is an image of the bead-type BB cream prepared in Manufacturing Example 1 after eight weeks at 50° C.

Disclosed is a pact-type cosmetic wherein the bead-type liquid foundation cosmetic composition is 0.1-1.0% w/v gel forming material; 10-20% w/v oil component; 50-60% w/v water component; 1-10% w/v thickener; 1-10% w/v coloring agent; and 15-25% w/v emulsifier. The pact-type cosmetic is disposed in a cosmetic container having a body and a lid, in which a mesh is disposed on the top of the body of the cosmetic composition. FIG. 1 is a schematic of the disclosed pact-type cosmetic and a cosmetic container.

The bead-type liquid foundation cosmetic composition can have 0.1, 0.2, 0.3, 0.4, 0.5, 0.6, 0.7, 0.8, 0.9, or 1.0% w/v gel forming material or a range of such amounts.

The bead-type liquid foundation cosmetic composition can have 10, 11, 12, 13, 14, 15, 16, 17, 18, 19, or 20% w/v oil component, or a range of such amounts.

The bead-type liquid foundation cosmetic composition cosmetic can have 50, 51, 52, 53, 54, 55, 56, 57, 58, 59, or 60% w/v water component, or a range of such amounts.

The bead-type liquid foundation cosmetic composition cosmetic can have 1, 2, 3, 4, 5, 6, 7, 8, 9, or 10% w/v thickener, or a range of such amounts.

The bead-type liquid foundation cosmetic composition can have 1, 2, 3, 4, 5, 6, 7, 8, 9, or 10% w/v coloring agent, or a range of such amounts.

The bead-type liquid foundation cosmetic composition can have 15, 16, 17, 18, 19, 20, 21, 22, 23, 24, or 25% w/v emulsifier, or a range of such amounts.

The gel forming material can be xanthan gum, traganth gum, guar gum, or garrageenan. The disclosed gel forming materials can be used individually or in combination.

The oil component can be cyclopentasiloxane, Mangifera Indica (Mango) seed butter, triethoxycaprylylsilane, methyl methacrylate crosspolymer, aluminum hydroxide, caprylyl glycol, tocopheryl acetate, or zinc oxide. The disclosed oil components can be used individually or in combination.

The water component can be water, butylene glycol, panthenol, hydrogenated poly ($C_{6-14}$ olefin) polymers, glycerin, allantoin, caprylhydroxamic acid, agar, disodium EDTA, ethylhexylglycerin, niacinamide, or adenosine. The disclosed water components can be used individually or in combination.

The thickener can be hydroxyethyl acrylate/sodium acryloyldimethyl taurate copolymer in which the percentage of hydroxyethyl acrylate monomers is 35-40%, hydroxyethyl acrylate/sodium acryloyldimethyl taurate copolymer in which the percentage of sodium acryloyldimethyl taurate monomers is 35-40%, acrylate/C10-30 alkyl acrylate crosspolymer, or hydroxyethylcellulose. The disclosed thickeners can be used individually or in combination.

The coloring agent can be yellow iron oxide (Cl 77492), red iron oxide (Cl 77491), black iron oxide (Cl 77499), or mica. The disclosed thickeners can be used individually or in combination.

The emulsifier can be cetearyl alcohol, sorbitan isostearate, polysorbate 80, glyceryl stearate, PEG-100 stearate, potassium olivate, polysorbate 60, or decyl glucoside. The disclosed emulsifiers can be used individually or in combination.

The bead-type liquid foundation cosmetic composition can additionally contain 3.5-50% w/v titanium dioxide, the UV blocking agent. The amount of titanium dioxide can be 3.5, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% w/v, or a range of such amounts. The bead-type liquid foundation cosmetic composition can further contain 1-30% w/v ethylhexyl methoxycinnamate, the discoloration preventive agent. The amount of ethylhexyl methoxycinnamate can be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% w/v, or a range of such amounts. The bead-type liquid foundation cosmetic composition can also contain 2-30% w/v squalane or cyclohexasiloxane, the skin conditioner. The amounts of squalane or cyclohexasiloxane can be 2, 3, 4, 5, 6, 7, 8, 9, 10, 11, 12, 13, 14, 15, 16, 17, 18, 19, 20, 21, 22, 23, 24, 25, 26, 27, 28, 29, or 30% w/v, or a range of such amounts. The bead-type liquid foundation cosmetic composition can still further contain 0.01-2% w/v triethaneolamine, the pH regulator. The amount of triethaneolamine can be 0.01, 0.05, 0.1, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, or 2.00% w/v, or a range of such amounts. The bead-type liquid foundation cosmetic composition can moreover contain 0.01-1% w/v fragrance. The amount of fragrance can be 0.01, 0.05, 0.1, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.00% w/v or a range of such amounts.

In the bead-type liquid foundation cosmetic composition, the bead diameter is 0.5-20 mm, preferably 0.7-10 mm, more preferably 1-9 mm, and most preferably 3-8 mm. The bead diameter can be 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0 mm or a range of such diameters. The bead-type liquid foundation cosmetic composition is preferably a cream.

In general, the viscosity required for a cosmetic composition is 500-2500 cp, and the viscosity of the bead-type liquid foundation cosmetic composition is 1800-2100 cp. If the bead diameter is less than 3 mm, the viscosity is preferably 500-1000 cp, and if the bead diameter is 3-4 mm, the viscosity can be 1500-2500 cp. If the bead size is 6-8 mm, the preferable viscosity is 800-2000 cp.

The content of a pigment required for the bead-type liquid foundation cosmetic composition can be 0.5-20 weight % by the total weight of the cosmetic composition, preferably 1-10 weight %, more preferably 1.5-8 weight %, and most preferably 2.0-5.0 weight %. The pigment can be a coloring agent.

The preferable pH range required for the bead-type liquid foundation cosmetic composition is 4-9, and more preferably 5-8. The pH can be 4.0, 4.5, 5.0, 5.5, 6.0, 6.5, 7.0, 7.5, 8.0, 8.5, or 9.0, or a range of such values.

Figure 6:
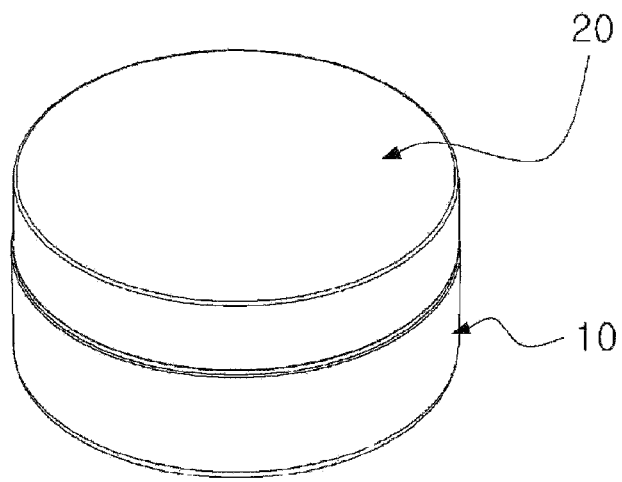
FIG. 6 is a perspective view of the disclosed cosmetic container.
Figure 7:
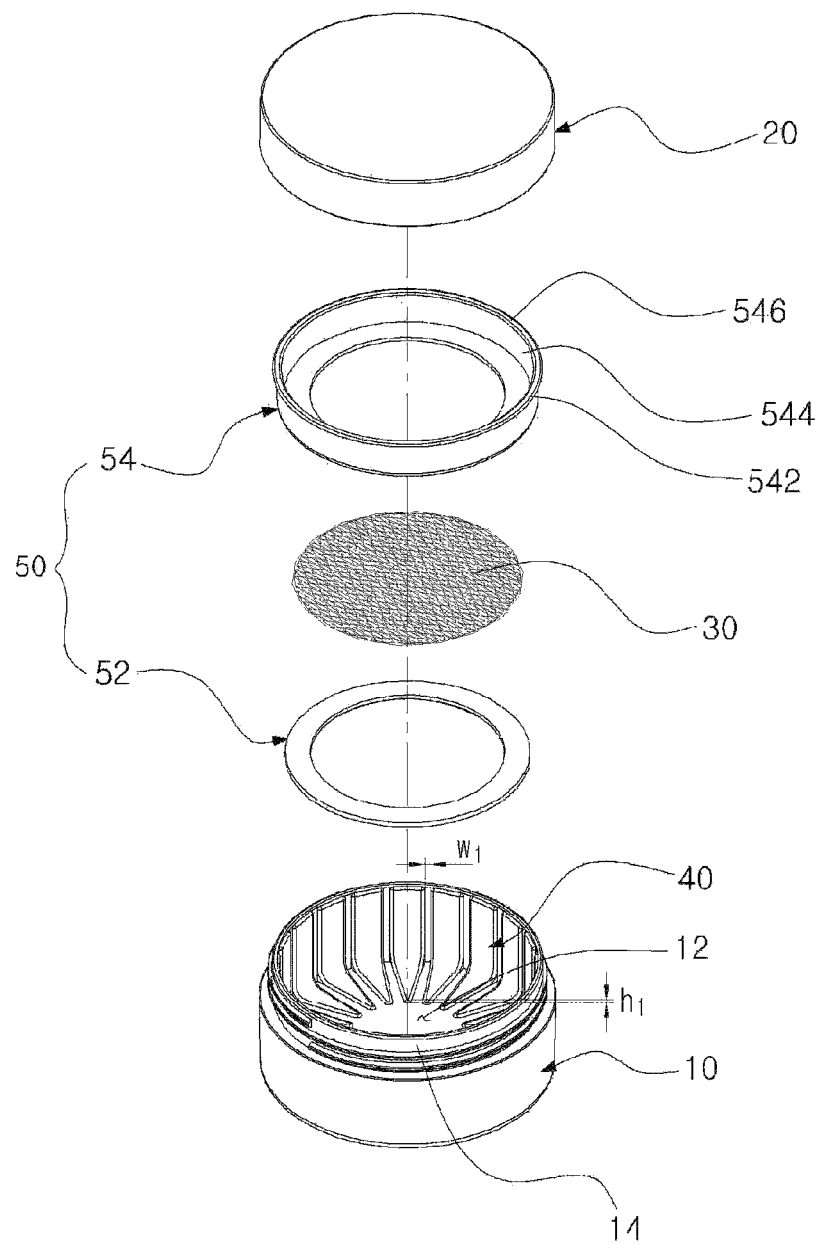
FIG. 7 is an exploded view of the disclosed cosmetic container.
Figure 8:
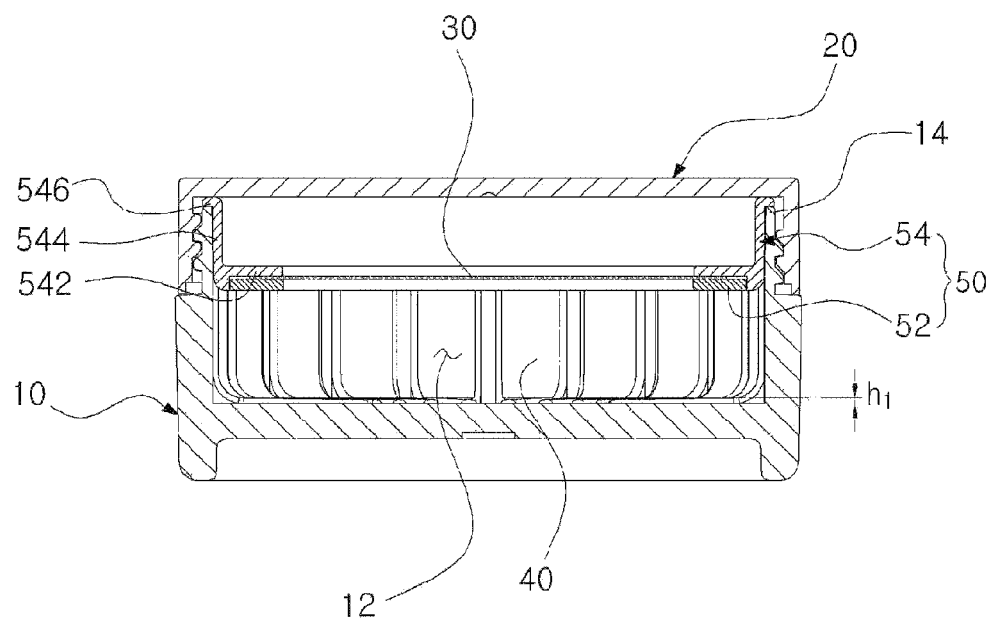
FIG. 8 is a sectional view of the disclosed cosmetic container.
Figure 9:
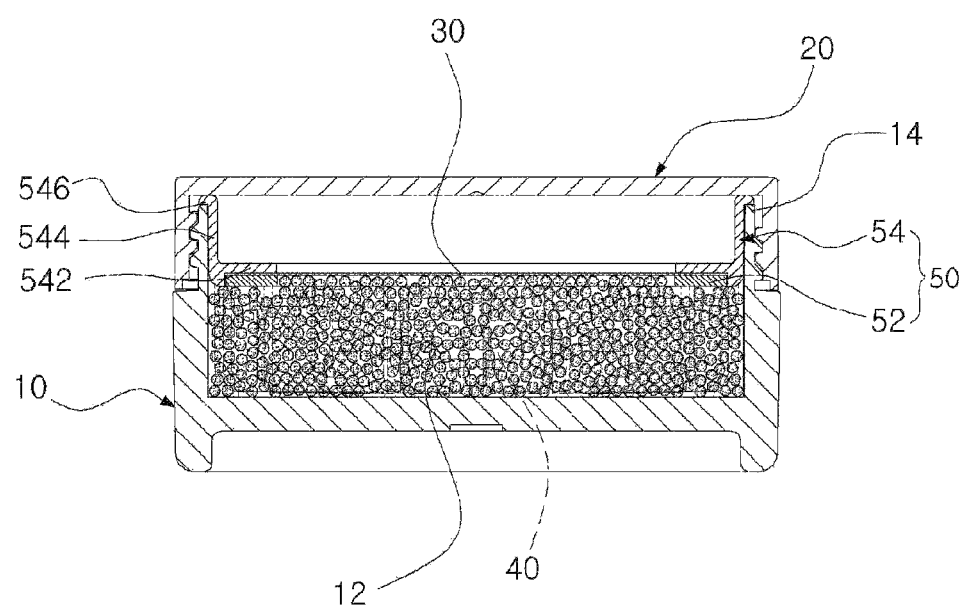
FIG. 9 is a sectional view of the disclosed pact-type cosmetic disposed within the body of the cosmetic container.
Figure 10:
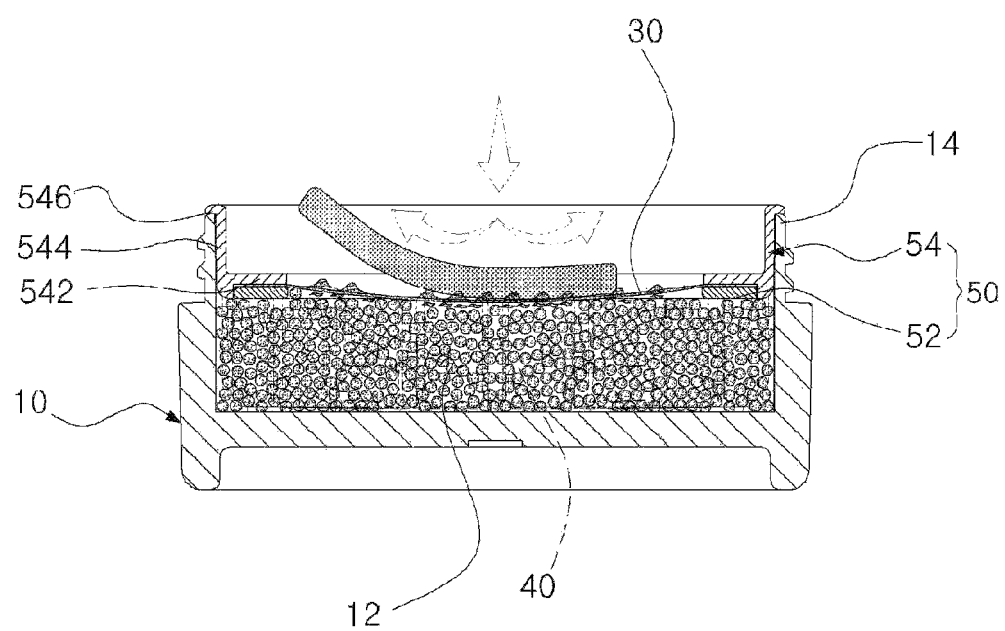
FIG. 10 is a sectional view of the disclosed pact-type cosmetic disposed within the body of the cosmetic container in which the mesh within the cosmetic container is in contact with a scrubber.
Figure 11:
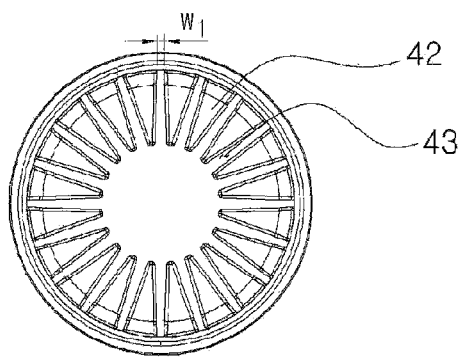
FIG. 11 is a set of plan views of the shapes of the disclosed protrusions in the body of the cosmetic container.
Figure 11:
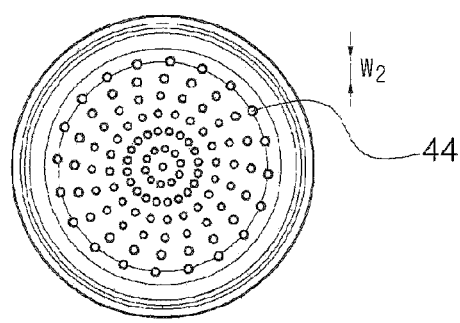
Figure 11:
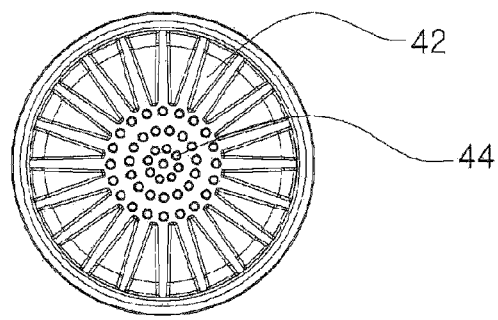
Figure 12:
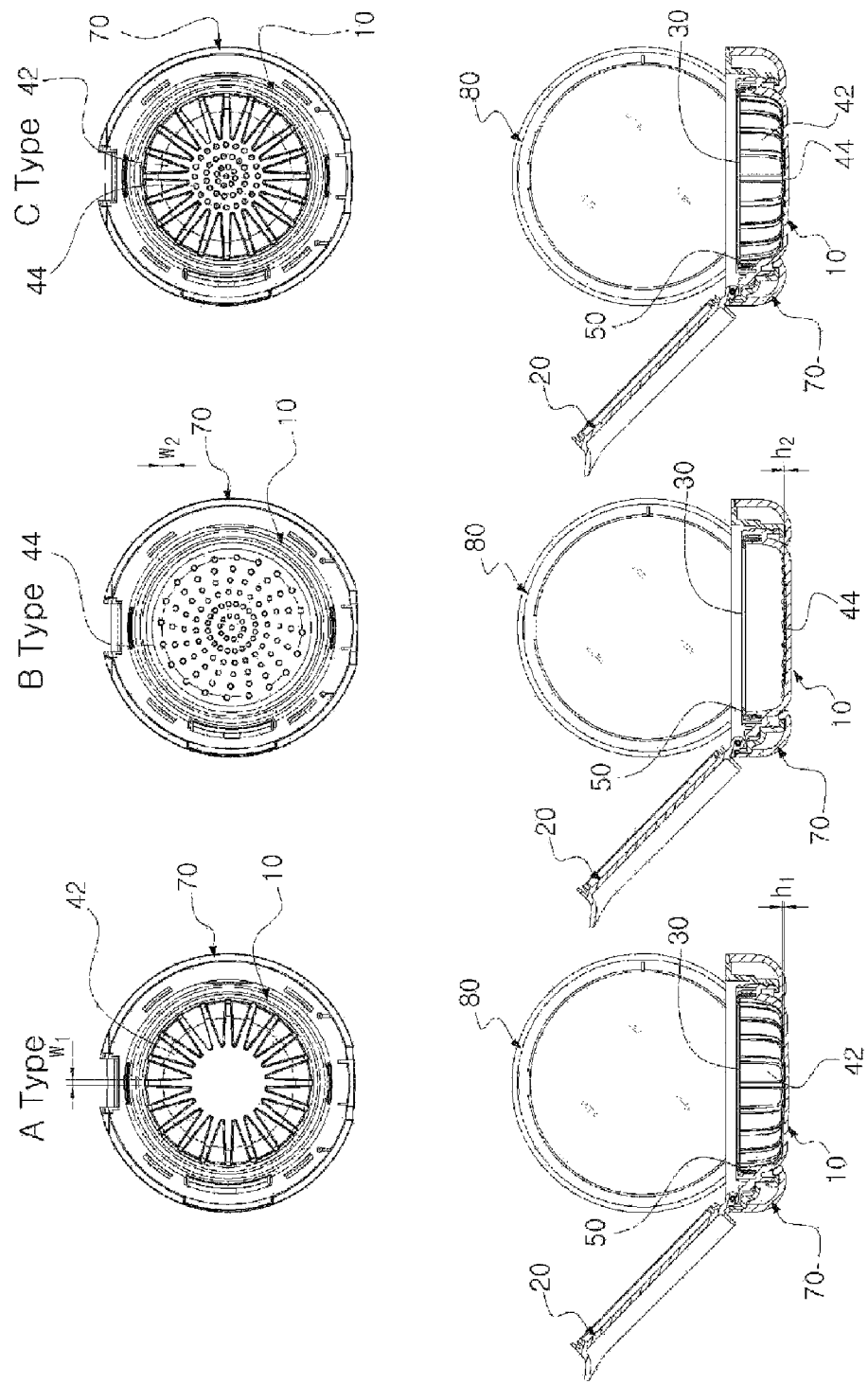
FIG. 12 is a set of plan views of the disclosed protrusions in the base of the cosmetic container and sectional views of the body and lid of the cosmetic container.

FIG. 6 is a perspective view of the disclosed cosmetic container; FIG. 7 is an exploded view of the disclosed cosmetic container; FIG. 8 is a sectional view of the cosmetic container; FIG. 9 is a sectional view of the disclosed pact-type cosmetic disposed within the body of the cosmetic container; FIG. 10 is a sectional view of the disclosed pact-type cosmetic disposed within the body of the cosmetic container in which a mesh within the body of the cosmetic container is in contact with a scrubber; FIG. 11 is a set of plan views of the shapes of the disclosed protrusions in the body of the cosmetic container; and FIG. 12 is a set of plan views of the disclosed protrusions in the base of the cosmetic container and sectional views of the body and lid of the cosmetic container.

The cosmetic container can prevent movement of the bead-type liquid foundation cosmetic composition of the invention. The cosmetic container has a container body (10); a lid (20); and a mesh (30) disposed within the container body (10). The inner base of the body of the container (10) can have protrusions (40).

Inside the container body (10), there is a space (12) for the bead-type liquid foundation cosmetic composition.

There is an inlet (14) on the upper extremity of the container body (10). The inlet (14) may be the top of the container body (10). On the outer surface of the inlet (14), there is a screw thread is formed to connect the container body with the lid (20) by a screw. The screw thread is capable of connecting the lid (20) to the container body (20)

The lid (20) attached on top of the container body allows access to the container body (10). In the inner periphery of the lid (20), there is the inverse of a screw thread which is capable of being connected with the screw thread formed in the outer surface of the inlet (14) of the container body (10).

The mesh (30) is disposed in the interior of the upper part of the container body (10). Contact of a scrubber with the surface of the mesh (30) closest to the inlet (14) is capable of discharging the bead-type liquid foundation cosmetic composition from the container body (10).

The mesh (30) is attached to a mesh coupling member (50), and the mesh coupling member (50) is disposed on the inner surface of the container body (10). The mesh coupling member (50) has a mesh connecting ring (52) and the mesh fixing member (54).

The mesh connecting ring (52) is annular and is capable of being attached to the lower surface of the mesh net (30).

The mesh fixing member (54) has a joint part (542) capable of being attached to the mesh (30), an upper extension part (544) capable of being connected to the upper extremity of the joint part (542), and a horizontal extension part (546) capable of being connected to the outer side of the upper extension part (544).

The outer surface of the upper extension part (544) is capable of being attached to the inlet (14) of the container body (10) and the horizontal extension part (546) is capable of being placed on an outer surface of the inlet (14) of the container body (10).

The mesh (30) is preferably capable of being attached between the mesh connecting ring (52) and the mesh fixing member (54) by thermal bonding, ultrasonic bonding, or high frequency bonding.

The inner surface of the container body (10) can have protrusions (40).

As shown in FIG. 11 A type, the protrusions (40) can be radial protrusions (42) and can be disposed on the bottom of the inner surface of the container body (10).

The radial protrusions (42) can triangular crosssections. Two neighboring radial protrusions can form a line slot (43).

Radial protrusions (42) can be disposed at regular intervals on the bottom of the inner surface of the container body (10).

The protrusions (40) can also be spherical protrusions (44) on the bottom of the inner surface of the container body (10), as shown in FIG. 11 B type. The spherical protrusions (44) can have the cross-section of a circle or an ellipse.

The spherical protrusions (44) can be disposed from the center of the bottom of the inner surface of the container body (10) to the outer extremity of the inner surface of the container body (10) at regular intervals. The spherical protrusions (44) can be disposed so as form one or more concentric circles.

The protrusions (40) can be a combination of radial protrusions (42) and spherical protrusions (44) on the bottom of the inner surface of the container body (10), as shown in FIG. 11 C type. The spherical protrusions (44) can be in the center of the bottom of the inner surface of the container body (10), and the radial protrusions (42) can at least partially surround the circular protrusions (44).

The protrusions (40), either in the form of the radial protrusions (42) or in the form of the circular protrusions (44), can extend from the bottom of the inner surface of the container body (10) to the interior of the container body (10).

The height (h1) of the radial protrusions (42) and the height (h2) of the spherical protrusions (44) are independently the maximum heights of the radial protrusions (42) and spherical protrusions (44) above the bottom of the inner surface of the container body and are preferably 0.2 mm-2.0 mm. The height (h1) and height (h2) can independently be 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mm, or a range of any of such heights.

As disclosed herein, there are slots between the radial protrusions (42). The width of a slot (w1) is preferably 1.0-5.0 mm.

In addition, the width (w2) of the space between each circular protrusion (44) is preferably 1.0-5.0 mm. The width (w2) can be 1.0, 1.5, 2.0, 2.5, 3.0, 3.5, 4.0, 4.5, or 5.0 mm, or a range of such widths.

As shown in FIG. 12, the container body (10) may be disposed within an outer container (70). The outer container (70) can have an outer container lid (80) that can be connected to the outer container (70) by a hinge.

The method for assembling the cosmetic container to prevent the flow of the bead-type liquid foundation cosmetic composition according to an example of the present invention and the instruction for the use are explained hereinafter.

To assemble the cosmetic container, the mesh (30) is first attached to the mesh coupling member (50), as shown in FIGS. 7 and 8, and the mesh (30) is placed between the upper part of the mesh net connecting ring (52) and the joint part (542) of the mesh fixing part (54) by thermal bonding, ultrasonic bonding, or high frequency bonding.

The bead-type liquid foundation cosmetic composition is capable of filling the container body (10) having the protrusions for preventing movement (40) formed on the bottom floor of the container. The mesh net coupling member (50) having the mesh (30) connected thereto is attached to the upper part of the container body (10). The outer periphery of the upper extension part (544) of the mesh fixing part (54) is tightly connected to the inner periphery of the container body (10) and the horizontal extension part (546) is placed on the top of the inlet (14) of the container body (10).

Lastly, the lid (20) is connected to the container body (10). As a result, the cosmetic container designed to prevent the flow of the bead-type liquid foundation cosmetic composition of the invention is assembled.

When the protrusions (40) are formed in the inside of the compact container, the container body (10) assembled as described above is placed in the inside of the outer container (70) with the outer container lid (80) connected by hinge.

To use the cosmetic container designed to prevent the flow of the bead-type liquid foundation cosmetic composition which has been assembled as shown above, first the lid (20) is separated from the container body (10). As shown in FIG. 10, the top face of the mesh net (30) is scrubbed right and left with pressing with such a cosmetic tool as a puff. Then, the scrubbed liquid foundation cosmetic composition beads are broken and the cosmetic composition filled in the beads is discharged to the top of the mesh net (30).

When the protrusions for preventing movement (40) designed to prevent the flow of the bead-type liquid foundation cosmetic composition are formed in the compact container, the outer container lid (80) is first opened from the outer container (70), as shown in FIG. 12, and the lid (20) is opened from the container body (10). Next, the top face of the mesh net (30) is scrubbed right and left with pressing with such a cosmetic tool as a puff. Then, the scrubbed liquid foundation cosmetic composition beads are broken and the cosmetic composition filled in the beads is discharged to the top of the mesh net (30).

As the bead-type liquid foundation cosmetic composition is consumed, the cosmetic container has a space inside. Then, the bead-type liquid foundation cosmetic composition is moving around in the space freely, so even though the mesh net (30) is pressed the beads are not broken. Since the cosmetic container of the present invention designed to prevent the flow of the bead-type liquid foundation cosmetic composition has the protrusions for preventing movement (40) on the bottom floor of the container body (10) containing the bead-type liquid foundation cosmetic composition, the movement of the bead-type liquid foundation cosmetic composition is minimized whenever the mesh net (30) is scrubbed with a puff in any direction and accordingly the bead-type liquid foundation cosmetic composition can be easily broken out.

To use the cosmetic composition contained in the conventional cushion compact containing urethane foam, a puff is used to press the urethane foam and the stained composition in the puff is spread on the skin. At this time, about 20% of the cosmetic composition included in the urethane foam is not smeared onto the puff, suggesting that a large amount of the cosmetic composition is lost.

On the contrary, the cosmetic composition prepared in Examples 1-4 are filled in the cosmetic container of the invention and used by a puff provided from the cosmetic container, most of the BB cream filled in the cosmetic container along the bottom structure is smeared onto the puff so that the BB cream is hardly wasted, indicating the container of the invention is advantageous in saving BB cream.

The cosmetic comprising a cosmetic composition of bead-type liquid foundation filled in a mesh equipped cosmetic container maintains portability as the conventional cushion-type cosmetic has and at the same time is more advantageous in preventing the loss of cosmetic ingredients because urethane foam is not used as a carrier for the cosmetic composition herein.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Manufacturing Example 1

Preparation of Bead-Type BB Cream 1

The compounds listed in Table 1 below are mixed at the proper ratio of weight % (w/w) suggested in the Table to prepare bead-type BB cream through the following steps 1-5 shown below.

TABLE 1

| | Composition | Weight % (w/w) |
|---|---|---|
| 1 (oil phase | cyclopentasiloxane | 3.00 |
| | mango seed butter | 3.00 |

TABLE 1-continued

| | Composition | Weight % (w/w) |
|---|---|---|
| dissolver) | triethoxycaprylylsilane | 2.00 |
| | methyl methacrylate crosspolymer | 2.00 |
| | aluminum hydroxide | 2.00 |
| | caprylyl glycol | 2.00 |
| | tocopheryl acetate | 0.10 |
| 2 | titanium dioxide | 9.00 |
| 3 | ethylhexyl methoxycinnamate | 3.00 |
| 4 | squalane | 3.00 |
| 5 | yellow iron oxide (Cl 77492) | 0.47 |
| | red iron oxide (Cl 77491) | 0.17 |
| | black iron oxide (Cl 77499) | 0.14 |
| | fragrance | 0.10 |
| 6 | cyclohexasiloxane | 3.00 |
| 7 | Mica | 3.00 |
| 8 | triethanolamine | 0.20 |
| 9 | purified water | 10.05 |
| (water phase | butylene glycol | 15.00 |
| dissolver) | panthenol | 3.00 |
| | hydrogenated poly($C_{6-14}$ olefin) polymer | 3.00 |
| | glycerin | 2.00 |
| | allantoin | 0.10 |
| | caprylhydroxamic acid | 0.05 |
| | agar | 1.00 |
| | disodium EDTA | 0.02 |
| 10 | cetearyl alcohol | 3.00 |
| (emulsifier) | sorbitan isostearate | 3.00 |
| | polysorbate 80 | 3.00 |
| | glyceryl stearate | 2.00 |
| | PEG-100 stearate | 2.00 |
| | potassium olivate | 2.00 |
| | polysorbate 60 | 2.00 |
| 11 | purified water | 10.00 |
| 12 | hydroxyethyl acrylate/sodium acryloyldimethyltaurate copolymer (35-40%) | 2.00 |
| 13 | acrylate/$C_{10-30}$alkyl acrylate crosspolymer | 0.20 |
| 14 | hydroxyethylcellulose | 0.20 |
| 15 | xanthan gum | 0.20 |

Step 1: The water phase dissolver (9) raw materials were heated up to 90° C. and dissolved, which were transferred in a main mixer.

Step 2: The oil phase dissolver (1) raw materials were heated up to 72-74° C. and dissolved, to which titanium dioxide (2), ethylhexyl methoxycinnamate (3), squalane (4), [iron oxide (Cl 77492), iron oxide (Cl 77491), iron oxide (Cl 77499), fragrance] (5), cyclohexasiloxane (6), Mica (7), and triethanolamine (8) were added, followed by homogenization. An emulsifier (10) was added thereto and the mixture was transferred in the main mixer with maintaining the temperature at 68-70° C.

Step 3: The materials loaded in step 1 and step 2 were emulsified. Purified water (11) was added to the mixer. Hydroxyethyl acrylate/sodium acryloyldimethyl taurate copolymer (35-40%) (12), acrylate/C10-30 alkyl acrylate crosspolymer (13), hydroxyethylcellulose (14), and xanthan gum (15) were dispersed therein. The prepared liquid mixture was loaded in the main mixer, followed by emulsification. The temperature was maintained at 70° C.

Step 4: The liquid prepared in step 3 was spilled on silicon oil at the temperature of under 10° C. drop by drop for cooling.

Step 5: The bead-type BB cream cooled down in step 4 was obtained.

The bead-type BB cream prepared by the steps 1 to 5 above was confirmed to have the size of 2-3 mm and the composition composed by the indicated each weight % (w/w) shown in Table 1.

In Table 1, the oil phase dissolver (1) is an oil component; the titanium dioxide (2) is a UV blocking agent; the ethylhexyl methoxycinnamate (3) is a discoloration preventive agent; the squalane (4) is a skin conditioner; the [iron oxide (Cl 77492), iron oxide (Cl 77491), iron oxide (Cl 77499), fragrance] (5) is a coloring agent; the cyclohexasiloxane (6) is a skin conditioner; the Mica (7) is a coloring agent; the triethanolamine (8) is a pH regulator; the water phase dissolver (9) is a water component; the emulsifier (10) is an emulsifier; the purified water (11) is a water component; the hydroxyethyl acrylate/sodium acryloyldimethyl taurate copolymer (35-40%) (12), the acrylate/C10-30 alkyl acrylate crosspolymer (13), and the hydroxyethylcellulose (14) are thickeners; and the xanthan gum (15) is a gel forming material.

Manufacturing Example 2

Preparation of Bead-Type BB Cream 2

The bead-type BB cream in the size of 2-3 mm was prepared by the same manner as described in Manufacturing Example 1 except that 1.14 weight % of black iron oxide (Cl 77499) and 8.00 weight % of titanium dioxide were used.

Herein, the concentrations of at least one of pigments selected from the group consisting of yellow iron oxide, red iron oxide, black iron oxide, and titanium dioxide, which are added to express diverse skin colors according to race and region, can be regulated at different ratios.

Manufacturing Example 3

Preparation of Bead-Type BB Cream 3

The bead-type BB cream was prepared by the following steps 1-5 by using the compounds listed in Table 2 below at the ratios of suggested weight %.

TABLE 2

| | | Composition | Weight % (w/w) |
|---|---|---|---|
| 1 | | cyclopentasiloxane | 2.00 |
| (oil phase dissolver) | | mango seed butter | 2.00 |
| | | triethoxycaprylylsilane | 2.00 |
| | | methyl methacrylate crosspolymer | 2.00 |
| | | aluminum hydroxide | 2.00 |
| | | caprylyl glycol | 0.10 |
| | | tocopheryl acetate | 0.10 |
| | | zinc oxide | 0.98 |
| 2 | | titanium dioxide | 8.08 |
| 3 | | ethylhexyl methoxycinnamate | 5.00 |
| 4 | | squalane (squalane) | 2.00 |
| 5 | | isoamyl p-methoxycinnamate | 2.00 |
| 6 | | yellow iron oxide (Cl 77492) | 0.90 |
| | | red iron oxide (Cl 77491) | 0.18 |
| | | black iron oxide (Cl 77499) | 0.08 |
| | | fragrance (fragrance) | 0.10 |
| 7 | | cyclohexasiloxane | 2.00 |
| 8 | | Mica (Mica) | 2.00 |
| 9 | | triethanolamine | 0.20 |
| 10 | | purified water | 17.32 |
| (water phase dissolver) | | butylene glycol | 15.00 |
| | | panthenol | 0.30 |
| | | hydrogenated poly($C_{6-14}$ olefin) polymer | 2.00 |
| | | ethylhexylglycerin | 0.10 |
| | | allantoin | 0.10 |
| | | agar (agar) | 1.00 |
| | | disodium EDTA | 0.02 |
| | | niacinamide | 2.00 |
| | | adenosine | 0.04 |
| 11 | | cetearyl alcohol | 2.00 |
| (emulsifier) | | sorbitan isostearate | 2.00 |
| | | polysorbate 80 | 2.00 |
| | | glyceryl stearate | 2.00 |
| | | PEG-100 stearate | 2.00 |
| | | potassium olivate | 2.00 |
| | | polysorbate 60 | 2.00 |
| 12 | | purified water | 10.00 |
| 13 | | hydroxyethyl acrylate/sodium acryloyldimethyltaurate copolymer (35-40%) | 2.00 |
| 14 | | acrylate/$C_{10-30}$alkyl acrylate crosspolymer | 0.20 |
| 15 | | hydroxyethylcellulose | 2.00 |
| 16 | | xanthan gum | 0.20 |

Step 1: The water phase dissolver (10) raw materials were heated up to 90° C. and dissolved, which were transferred in a main mixer.

Step 2: The oil phase dissolver (1) raw materials were heated up to 72-74° C. and dissolved, to which titanium dioxide (2), ethylhexyl methoxycinnamate (3), squalane (4), isoamyl p-methoxycinnamate (5), [iron oxide (Cl 77492), iron oxide (Cl 77491), iron oxide (Cl 77499), fragrance] (6), cyclohexasiloxane (7), Mica (8), and triethanolamine (9) were added, followed by homogenization. An emulsifier (11) was added thereto and the mixture was transferred in the main mixer with maintaining the temperature at 68-70° C.

Step 3: The materials loaded in step 1 and step 2 were emulsified. Purified water (12) was added to the mixer. Hydroxyethyl acrylate/sodium acryloyldimethyl taurate copolymer (35-40%) (13), acrylate/C10-30 alkyl acrylate crosspolymer (14), hydroxyethylcellulose (15), and xanthan gum (16) were dispersed therein. The prepared liquid mixture was loaded in the main mixer, followed by emulsification. The temperature was maintained at 70° C.

Step 4: The liquid prepared in step 3 was spilled on silicon oil at the temperature of under 15° C. drop by drop for cooling.

Step 5: The bead-type BB cream cooled down in step 4 was obtained.

The bead-type BB cream prepared by the steps 1-5 above was confirmed to have the size of 2-3 mm and the composition composed by the indicated each weight % (w/w) shown in Table 2.

In Table 2, the oil phase dissolver (1) is an oil component; the titanium dioxide (2) is a UV blocking agent; the ethylhexyl methoxycinnamate (3) is a discoloration preventive agent; the squalane (4) is a skin conditioner; the isoamyl p-methoxycinnamate (5) is a UV blocking agent (blocking UV B); the [iron oxide (Cl 77492), iron oxide (Cl 77491), iron oxide (Cl 77499), fragrance] (6) is a coloring agent; the cyclohexasiloxane (7) is a skin conditioner; the Mica (8) is a coloring agent; the triethanolamine (9) is a pH regulator; the water phase dissolver (10) is a water component; the emulsifier (11) is an emulsifier; the purified water (12) is a water component; the hydroxyethyl acrylate/sodium acryloyldimethyl taurate copolymer (35-40%) (13), the acrylate/C10-30 alkyl acrylate crosspolymer (14), and the hydroxyethylcellulose (15) are thickeners; and the xanthan gum (16) is a gel forming material.

Manufacturing Example 4

Preparation of Bead-Type BB Cream 4

The bead-type BB cream in the size of 2-3 mm was prepared by the same manner as described in Manufacturing Example 3 except that methylene bis-benzotriazolyltetramethylbutylphenol was used instead of isoamyl p-methoxycinnamate (5), decyl glucoside was added at the concentration of 2.00 weight % as an emulsifier (11), and purified water was added at the concentration of 8.00 weight % herein.

Manufacturing Example 5

Preparation of Cosmetic Container

The cosmetic container was provided from Tolykorea, Co., Ltd.

Example 1

Preparation of Pact-Type Cosmetic 1

A pact-type cosmetic was prepared by filling the bead-type BB cream prepared in Manufacturing Example 1 in the cosmetic container prepared in Manufacturing Example 5.

Example 2

Preparation of Pact-Type Cosmetic 2

A pact-type cosmetic was prepared by filling the bead-type BB cream prepared in Manufacturing Example 2 in the cosmetic container prepared in Manufacturing Example 5.

Example 3

Preparation of Pact-Type Cosmetic 3

A pact-type cosmetic was prepared by filling the bead-type BB cream prepared in Manufacturing Example 3 in the cosmetic container prepared in Manufacturing Example 5.

Example 4

Preparation of Pact-Type Cosmetic 4

A pact-type cosmetic was prepared by filling the bead-type BB cream prepared in Manufacturing Example 4 in the cosmetic container prepared in Manufacturing Example 5.

Experimental Example 1

Evaluation of Uniformity of Bead-Type BB Cream

To evaluate the uniformity of the bead-type BB creams prepared in Manufacturing Examples 1-4, the creams were applied on the skin and scrubbed thereon by hand. As a result, the bead-type BB creams prepared in Manufacturing Examples 1-4 were evenly applied on the skin without any stain or impurities with expressing even color expression with showing excellent skin cover effect.

Experimental Example 2

Evaluation of Temperature Stability of Bead-Type BB Cream

The following experiment was performed to investigate whether or not the bead shape of the BB creams prepared in Manufacturing Examples 1-4 of the invention was maintained well at room temperature and at a high temperature.

Particularly, the bead-type BB cream prepared in Manufacturing Example 1 was filled in a transparent plastic container, which was instantly exposed on the surrounding temperature of 25° C. or 50° C. for 8 weeks, during which the beads were observed. The results are shown in FIGS. 2-5.

As shown in FIGS. 2-5, the bead-type BB creams maintained their bead shape at room temperature and at a high temperature even after a long while, suggesting that they had excellent temperature stability.

BRIEF DESCRIPTION OF THE REFERENCE NUMBERS IN THE DRAWINGS

10: container body
12: space for capsule cosmetic
20: container lid
30: mesh
40: protrusions
42: radial protrusions
44: spherical protrusions
50: mesh net coupling member
52: mesh net connecting ring
54: mesh net fixing part
70: outer container
80: outer container lid
h1: height of radial protrusions
h2: height of spherical protrusions
w1: width of slots
w2: concentric circle width

What is claimed is:

1. A pact-type cosmetic comprising a bead-type liquid foundation cosmetic composition,
wherein the bead-type liquid foundation cosmetic composition is in the form of beads which consists of
0.1-1.0% w/v a gel forming material;
10-20% w/v a first phase that is one or more compounds selected from the group consisting of cyclopentasiloxane, Mangifera Indica (mango) seed butter, triethoxycaprylylsilane, methyl methacrylate crosspolymer, aluminum hydroxide, caprylyl glycol, tocopheryl acetate, and zinc oxide;
50-60% w/v a second phase that is one or more compounds selected from the group consisting of water, butylene glycol, panthenol, hydrogenated poly($C_{6-14}$ olefin) polymer, glycerin, allantoin, caprylhydroxamic acid, agar, disodium EDTA, ethylhexylglycerin, niacinamide, and adenosine;
1-10% w/v a thickener;
1-10% w/v a coloring agent; and
15-25% w/v an emulsifier, and
is filled in a cosmetic container covered by a mesh net equipped on top of the container body.

2. The pact-type cosmetic according to claim 1, wherein the gel forming material is one or more compounds selected from the group consisting of xanthan gum, agar, traganth gum, guar gum, and carrageenan.

3. The pact-type cosmetic according to claim 1, wherein the thickener is one or more compounds selected from the group consisting of hydroxyethyl acrylate/sodium acryloyldimethyl taurate copolymer (35-40%), acrylate/$C_{10-30}$ alkyl acrylate crosspolymer, and hydroxyethylcellulose.

4. The pact-type cosmetic according to claim 1, wherein the coloring agent is one or more compounds selected from the group consisting of yellow iron oxide (Cl 77492), red iron oxide (Cl 77491), black iron oxide (Cl 7499), and Mica.

5. The pact-type cosmetic according to claim 1, wherein the emulsifier is one or more compounds selected from the group consisting of cetearyl alcohol, sorbitan isostearate, polysorbate 80, glyceryl stearate, PEG-100 stearate, potassium olivate, polysorbate 60, and decyl glucoside.

6. The pact-type cosmetic according to claim 1, wherein the size of the beads is 0.5-20 mm.

7. The pact-type cosmetic according to claim 1, wherein the size of the beads is 3-8 mm.

8. The pact-type cosmetic according to claim 1, wherein the viscosity of the cosmetic composition is 500-2500 cp.

9. The pact-type cosmetic according to claim 1, wherein the pH of the cosmetic composition is 4-9.

10. A pact-type cosmetic comprising a bead-type liquid foundation cosmetic composition, wherein the bead-type liquid foundation cosmetic composition is in the form of beads which consists of 0.1-1.0% w/v a gel forming material;

10-20% w/v a first phase that is one or more compounds selected from the group consisting of cyclopentasiloxane, Mangifera Indica (mango) seed butter, triethoxycaprylylsilane, methyl methacrylate crosspolymer, aluminum hydroxide, caprylyl glycol, tocopheryl acetate, and zinc oxide;

50-60% w/v a second phase that is one or more compounds selected from the group consisting of water, butylene glycol, panthenol, hydrogenated poly($C_{6-14}$ olefin) polymer, glycerin, allantoin, caprylhydroxamic acid, agar, disodium EDTA, ethylhexylglycerin, niacinamide, and adenosine;

3.5-22% w/v titanium dioxide;

1-10% w/v a thickener;

1-10% w/v a coloring agent; and 15-25% w/v an emulsifier, and is filled in a cosmetic container covered by a mesh net equipped on top of the container body.

\* \* \* \* \*